United States Patent
Kmiec, Jr.

(10) Patent No.: US 9,427,266 B2
(45) Date of Patent: Aug. 30, 2016

(54) BUMP CUT ON HOLE EDGE

(71) Applicant: SYNTHES USA, LLC, West Chester, PA (US)

(72) Inventor: Stanley J. Kmiec, Jr., West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/788,328

(22) Filed: Mar. 7, 2013

(65) Prior Publication Data

US 2013/0274745 A1 Oct. 17, 2013

Related U.S. Application Data

(60) Provisional application No. 61/624,678, filed on Apr. 16, 2012.

(51) Int. Cl.
*A61B 17/56* (2006.01)
*A61B 17/72* (2006.01)
*A61B 17/74* (2006.01)

(52) U.S. Cl.
CPC .............. *A61B 17/72* (2013.01); *A61B 17/744* (2013.01); *A61B 17/7283* (2013.01)

(58) Field of Classification Search
CPC .............. A61B 17/72; A61B 17/7291; A61B 17/7233; A61B 17/1725; A61B 17/744
USPC ...................................................... 606/62–68
See application file for complete search history.

(56) References Cited

U.S. PATENT DOCUMENTS

| | | | |
|---|---|---|---|
| 6,409,768 B1* | 6/2002 | Tepic et al. | 623/23.27 |
| 7,763,022 B2 | 7/2010 | Speitling et al. | |
| 2004/0172027 A1 | 9/2004 | Speitling et al. | |
| 2010/0174284 A1 | 7/2010 | Schwammberger et al. | |
| 2010/0179551 A1* | 7/2010 | Keller et al. | 606/67 |

FOREIGN PATENT DOCUMENTS

| | | |
|---|---|---|
| EP | 1 452 144 | 9/2004 |
| WO | 2007/038560 | 4/2007 |
| WO | 2008/147975 | 12/2008 |
| WO | 2010/043380 | 4/2010 |
| WO | 2011/044917 | 4/2011 |

* cited by examiner

*Primary Examiner* — Mary Hoffman
*Assistant Examiner* — Tara R Carter
(74) *Attorney, Agent, or Firm* — Wayne C. Jaeschke, Jr.

(57) ABSTRACT

A bone fixation device includes an elongated body (a) having a first channel extending therethrough and configured for insertion into a bone, a first opening (b) formed on a first side wall of the body, the first side wall facing a lateral direction when implanted in a target orientation within the bone and a second opening (c) formed on a second side wall of the body opposite the first opening. A second channel (d) extends through the body from the first opening to the second opening and is dimensioned to permit insertion of an implant therethrough. A first bump (e) is positioned about a periphery of the first opening at a location at which a stress concentration would be a maximum if no such first bump were formed. The first bump is dimensioned to diffuse a concentration of stress about the periphery due to forces applied thereto by an implant extending through the second channel.

16 Claims, 5 Drawing Sheets

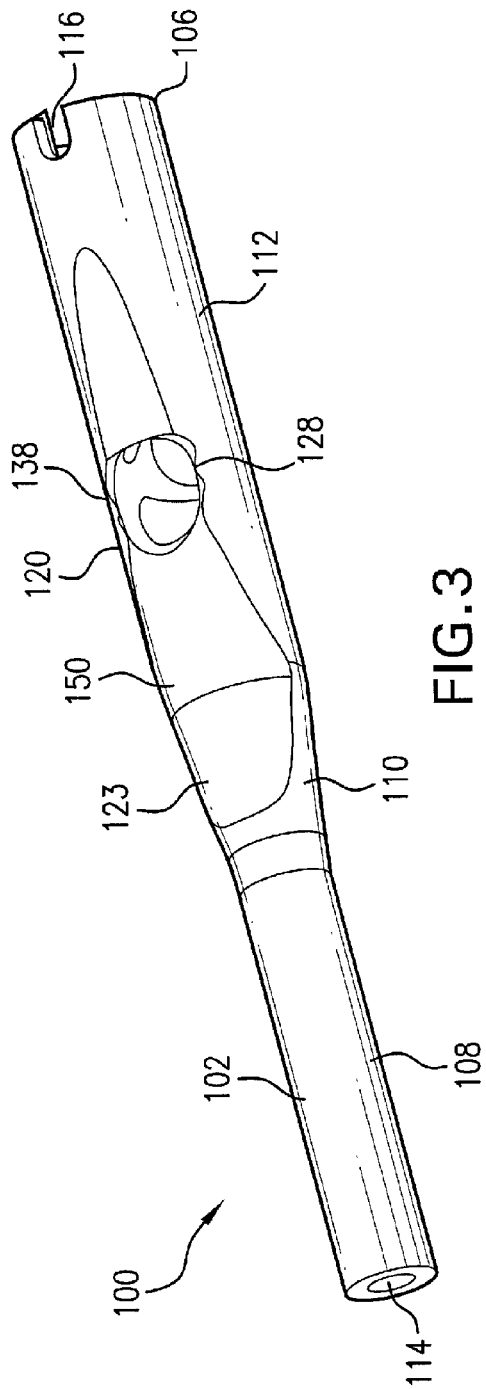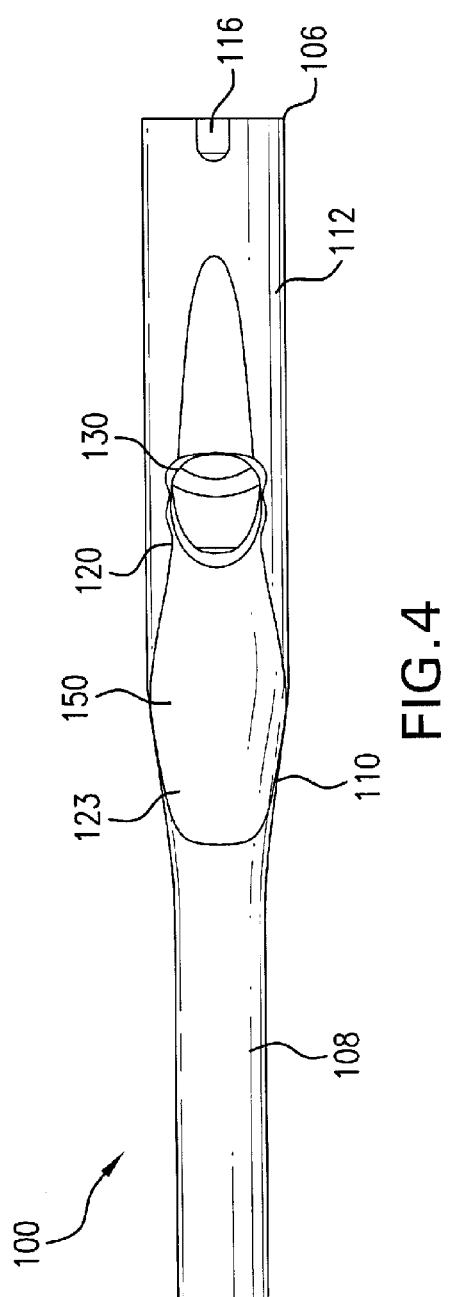

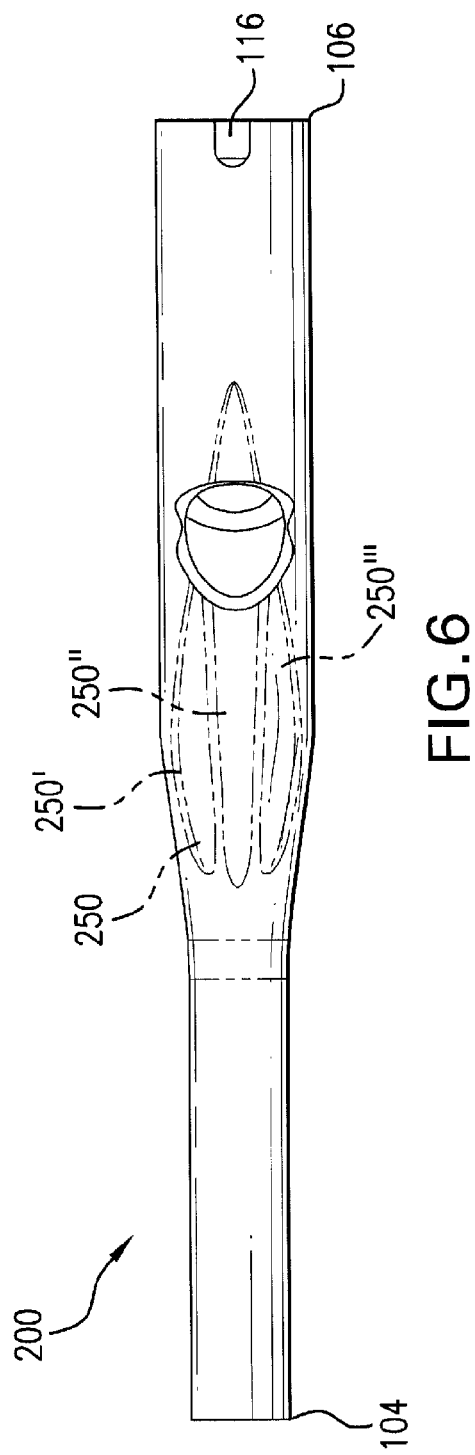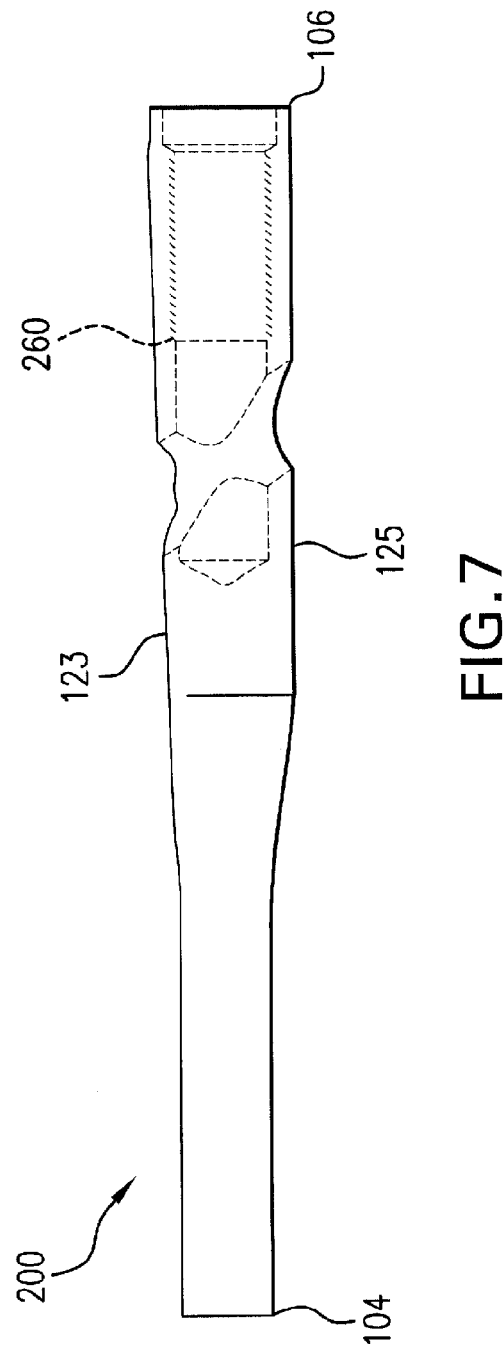

BUMP CUT ON HOLE EDGE

PRIORITY CLAIM

The present application claims priority to U.S. Provisional Appln. Ser. No. 61/624,678 entitled "Bump Cut on Hole Edge" filed on Apr. 16, 2012, the entire disclosure of which is incorporated herein by reference.

FIELD OF THE INVENTION

The present application is directed generally to devices and methods for bone fixation and, more particularly, to a bone fixation element configured for insertion into a fractured or otherwise damaged bone and subsequently locked thereto to support the bone in a desired configuration.

BACKGROUND INFORMATION

Systems and methods for bone fixation sometimes require the insertion of a bone fixation device into a bone to, for example, stabilize fragments of the bone in a desired alignment and/or to increase a strength of the bone. Certain portions of such intramedullary nails are more vulnerable to stress from the cyclic loading to which the nails are subjected. For example, intramedullary nails often include a transverse bore through which an implant may be passed into the trochanter. These implants applying cyclic loading to portions of the nail adjacent to the bore with each step the patient takes.

SUMMARY OF THE INVENTION

The present invention relates to a bone fixation device comprising an elongated body having a first channel extending therethrough from a proximal end to a distal end, the elongated body being configured and dimensioned for insertion into a bone, a first opening formed on a first side wall of the body, the first side wall being configured to face a lateral direction when implanted in a target orientation within the bone and a second opening formed on a second side wall of the body opposite the first opening. A second channel extends through the body from the first opening to the second opening, the second channel dimensioned to permit insertion of an implant therethrough. A first bump is positioned about a periphery of the first opening at a location at which a stress concentration would be at a maximum if no such first bump were formed, the first bump being dimensioned to diffuse a concentration of stress about the periphery due to forces applied thereto by an implant extending through the second channel.

BRIEF DESCRIPTION OF THE DRAWINGS

Several embodiments of the invention will be described in the following by way of example and with reference to the accompanying drawings in which:

FIG. 3 illustrates a second perspective view of the bone fixation device of FIG. 1;

FIG. 4 illustrates a third perspective view of the bone fixation device of FIG. 1;

FIG. 6 illustrates a perspective view of a bone fixation device according to an alternate embodiment of the invention;

FIG. 7 illustrates a partial cross-sectional view of the bone fixation device of FIG. 6;

DETAILED DESCRIPTION

Figure 1:
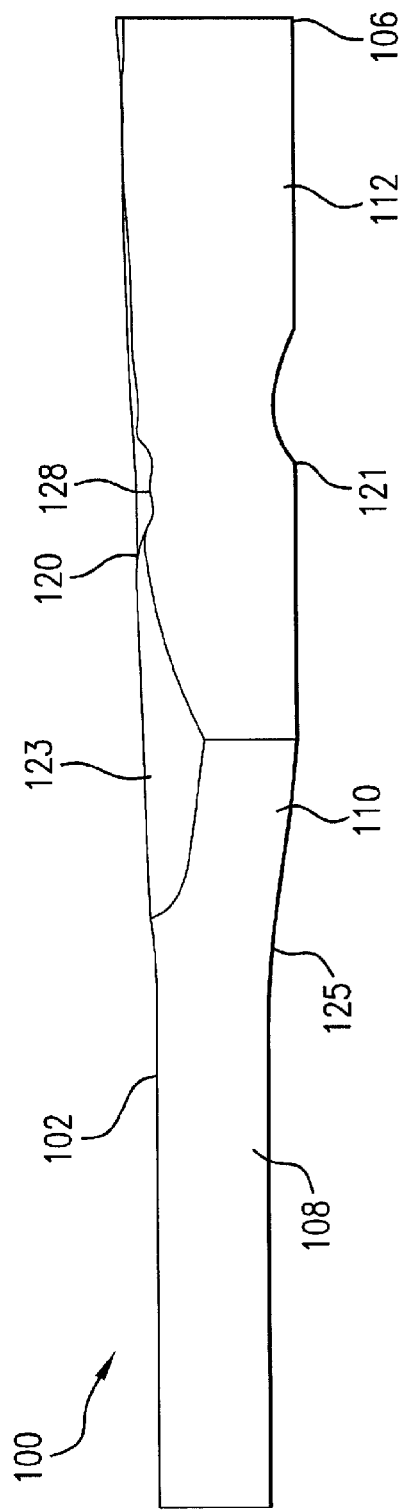
FIG. 1 illustrates a first perspective of a bone fixation device according to an exemplary embodiment of the invention.

The present invention is directed to a system and method for bone fixation comprising a bone fixation device configured for insertion into a bone (e.g., into a medullary cavity). Specifically, the bone fixation device according to the invention is formed as an intramedullary nail having a transverse bore extending therethrough to permit insertion of a trochanteric implant therethrough in accordance with an exemplary fixation procedure. The nail includes features configured to reduce concentrations of stress at specific locations therein. In an operative configuration, the nail according to the invention is implanted within a medullary canal of a bone (e.g., a femur) with a first wall thereof facing a lateral direction in the body while a second wall thereof faces medially. A transverse hole extends through the nail from the first side wall to the second side wall, as will be described in greater detail later on. The intramedullary nail further comprises an anterior surface which, when the nail is implanted as desired, faces an anterior direction and a posterior surface which faces a posterior direction. A portion of the first side wall may comprise cutouts (e.g., facets, etc.) reducing an outer profile of a portion of the nail which is to reside in a reduced clearance portion of the medullary canal or which is subject to an elevated level of stress during implantation or over the life of the implant. The transverse hole extends from a lateral opening on the first side wall to a medial opening on the second medial wall at a location and angle selected to aim an implant inserted therethrough along an axis of the femoral neck into the head of a femur into which the nail has been implanted. As will be described in more detail below, one or more stress reducing features are applied to the lateral opening of the transverse hole to diffuse stress concentrations that would otherwise result at locations around the lateral opening thereby enhancing the ability of the device to withstand the cyclic loadings to which it will be subjected. A first stress-reducing feature is formed as a portion of material of the device left in place as first and second regions surrounding the lateral opening are milled. Specifically, as will be described in greater detail later on, the first stress-reducing feature is defined on proximal and distal sides by first and second milled portions. A position of each of the first and second milled portions is selected to correspond to a location along the nail body at which a stress concentration would result about the periphery of the lateral opening if no such milled portions were provided. Thus, the first stress-reducing feature defined by the first and second milled portions serves as an elastic portion of the nail body capable of straining under excessive loads instead of fracturing, as will also be described in greater detail later on.

As will be described in greater detail later on, each of the first and second milled portions has a radius of curvature selected to conform to an amount of stress subjected to the lateral opening in a target configuration when implanted within the bone. In another embodiment, a second stress-reducing feature may be formed along a diametrically opposed wall of the first stress-reducing feature. The exemplary device according to the invention is usable within any bone in the body. Furthermore, the exemplary cutouts and transverse hole attributes disclosed herein may also be applied to any internal or external bone fixation device without deviating from the scope of the invention (e.g., a bone plate, etc.). It is further envisioned that the exemplary features of the nail according to the invention may be employed in both a right and left bone as well as bones having a wide range of anatomical lengths. It is noted that although the exemplary embodiment is disclosed with respect to a device configured for insertion into a femur, the exemplary system and method according to the invention may be employed in any other bone without deviating from the scope of the invention.

FIGS. 1-5 depict an exemplary bone fixation device 100 according to the present invention. The bone fixation device 100 according to this embodiment of the invention is an intramedullary nail. However, those skilled in the art will understand that the concepts of the invention may be applied as well to a bone plate or any other suitable fixation device. The device 100 comprises an elongated, substantially cylindrical body 102 extending from distal end (not shown) to a proximal end 106. A distal shaft 108 of the body 102 having a substantially constant outer diameter extends proximally from the distal end to a tapered portion 110. An outer diameter of the tapered portion 110 gradually increases from a minimum diameter at a distal end thereof substantially equal to the outer diameter of the distal shaft 108 to a maximum at a proximal end of the tapered portion 110. A proximal portion 112 extending proximally from the tapered portion 110 to the proximal end 106 has a substantially uniform outer diameter substantially equal to a diameter of the proximal end of the tapered portion 110. The increased outer diameter (relative to the distal shaft 108) enables the proximal portion 112 to permit the insertion of a trochanteric implant therethrough and to withstand the increased loading applied thereto, as those skilled in the art will understand. In an exemplary embodiment, a diameter of the first portion is approximately 10 mm. although any other dimensions may be used without deviating from the scope of the invention. A diameter of the second portion may be approximately 15-17 mm, although any other diameter may be used without deviating from the scope of the invention. A diameter of an elongated channel 114 extending through the cylindrical body 102 is selected to minimize the profile of the device while maintaining the strength of the body 102 at a level sufficient to withstand loads applied thereto in use. The proximal end 106 comprises one or more slots 116 (or other suitable structures) extending proximally thereinto for a predetermined distance. The slots 116 aid in attachment of the nail 100 to an insertion device (not shown), as those skilled in the art will understand. An inner wall of the proximal end 106 may be provided with a threading 118 configured, for example, to permit insertion of an end screw (not shown) thereinto, as those skilled in the art will understand. Those skilled in the art will understand that any known structure for coupling an insertion device to the nail may be included in the proximal end 106 without departing from the scope of the invention.

A first transverse opening 120 is provided on the lateral wall 123 of the body 102. The first transverse opening 120 opens into a channel 122 extending through the device 100 along a channel axis 124 to a second transverse opening 121 provided on a medial wall 125. In an exemplary embodiment, the channel 122 extends at an angle of approximately 56±0.5° relative to a longitudinal axis 126 of the device 100. It is noted, however, that any other angle may be employed (depending on the geometry of the bone to be treated) without deviating from the scope of invention. In one embodiment, the angle of the channel 122 relative to the longitudinal axis 100 may range from 50°-70°. For example, the angle of the channel 122 may be modified for insertion into the right or left femur, as those skilled in the art will understand, the angle being selected so that, once the device 100 has been implanted to a desired position within a bone, the channel 122 is angled to aim a trochanteric implant inserted therethrough along an axis of the neck of the bone into the head of the bone. However, as would be understood by those skilled in the art, the angle selected may be varied to achieve any desired path of the implant through the neck into the head of the bone.

Figure 2:
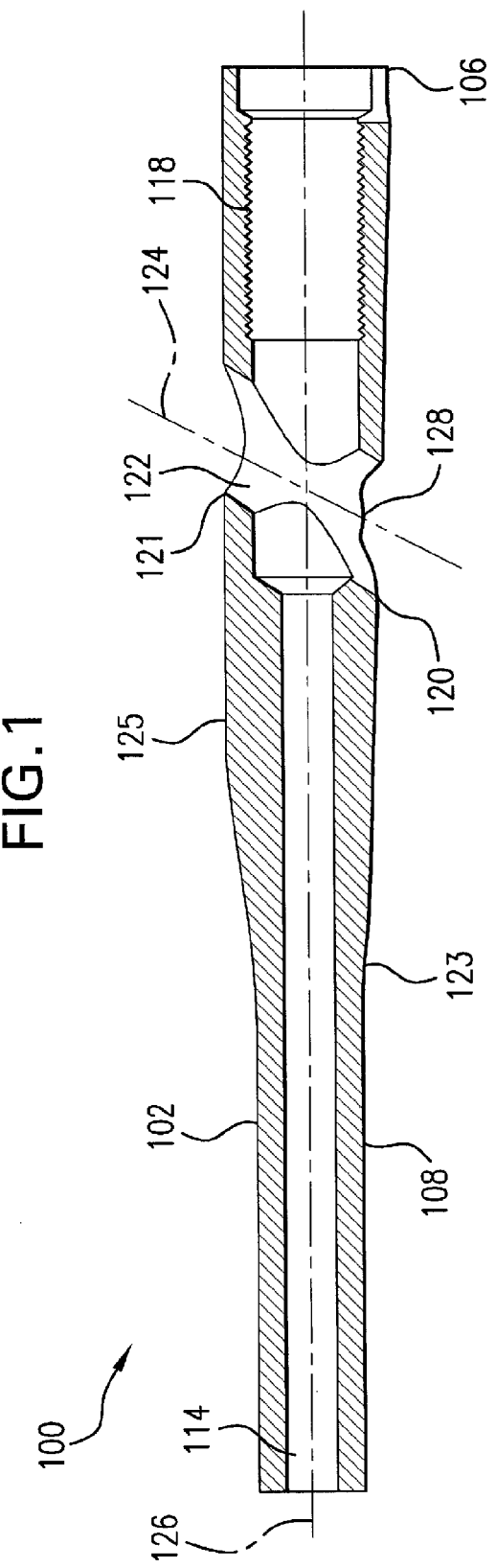
FIG. 2 illustrates a first partial cross-sectional view of the bone fixation device of FIG. 1.
Figure 5:
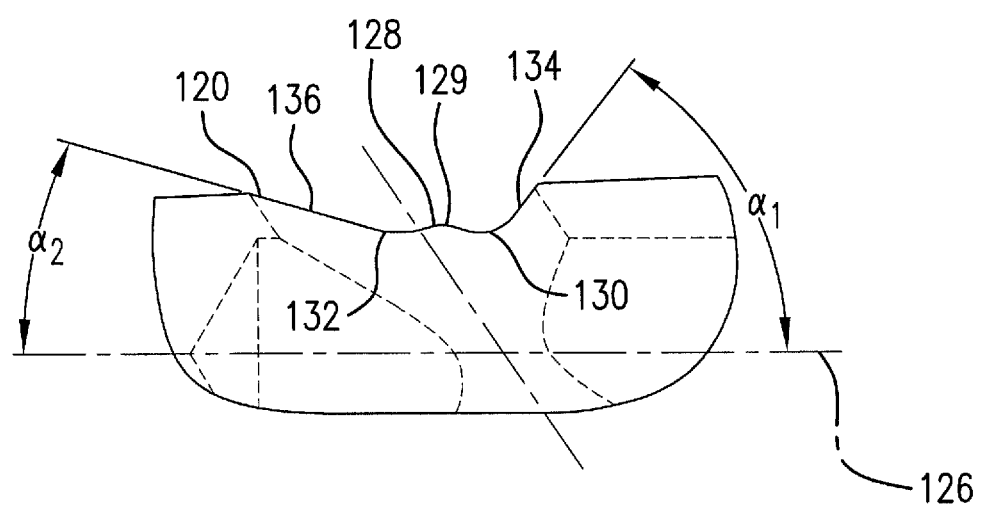
FIG. 5 illustrates a second partial cross-sectional view of the bone fixation device of FIG. 1.

As shown in FIGS. 1, 2 and 5, a periphery of the second transverse opening 121, which is under compression in an operative configuration, may be substantially smooth. A portion of the body 102 adjacent a periphery of the first opening 120, which is positioned toward the lateral wall 123 of the bone in an operative configuration, comprises first and second curved portions 130, 132 defining a first bump 128 therebetween. The first and second curved portions 130, 132 may be milled into the body 102, slightly enlarging the first opening, although any other forming technique may be used without deviating from the scope of the invention. Dimensions of each of the first and second curved portions 130, 132 and the first bump 128 are selected to disperse a concentration of stress which would be found at locations around the periphery of the opening 120 if the first opening 120 were left substantially oval around its perimeter (i.e., if the first opening were simply formed as the intersection of a cylindrical channel 122 with an outer surface of the body 102). The substantially arced shape of the first bump 128 defines an apex 129. A radius of curvature of each of the first and second curved portions 130, 132 and the location of the bump 128 are selected to conform to the stress distribution which would exist in a device not including these features under conditions to which the device is to be subjected. The curvature of the first and second portions 130, 132 may be symmetric or asymmetric as required to redistribute the stress as desired. In one embodiment, a first wall 134 extends at an angle of $\alpha_1$ relative to the longitudinal axis 126 of the device 100. In an exemplary embodiment, the angle $\alpha_1$ is between 50° and 60°, although any other angle may be used without deviating from the scope of the invention. A second wall 136 extends at an angle of $\alpha_2$ relative to the longitudinal axis 126 of the device 100. In an exemplary embodiment, the angle $\alpha_2$ is between 15° and 20°, although any other angle may be used without deviating from the scope of the invention. The angles $\alpha_1$ and $\alpha_2$ may be selected so there is no milling at proximal or distal walls of the opening 120 when drilling to a desired depth in the bone. In another embodiment, a second bump 138 may be provided on a side of the opening 120 opposite the first bump 128. The second bump 138 may be formed substantially similar to the first bump 128. It is further noted that any number of bumps may be provided around the first opening 120 to correspond a number of locations of stress concentration to which the device is subject when in an operative configuration, as will be described in greater detail later on.

The first and second bumps 128, 138 serve as an elastic portion of the nail 100, dispersing the stress concentration which would otherwise result in allowing the portion of the body 102 adjacent the opening 120 to expand and contract without fracturing, as those skilled in the art will understand. Specifically, when subjected to stress via a trochanteric implant, the first and second bumps 128, 138 are stretched at their respective apexes 129. Thus, a location of each apex 129 is selected to correspond to a location at which a stress concentration would result about the periphery of the first opening 120 if no such bumps 128, 138 were formed around the opening 120. The apexes 129 may be located in any position about the first opening 120 at which stress would have been concentrated. As those skilled in the art will understand, a trochanteric implant will cyclically load an intramedullary nail through which it is inserted (e.g., with each step a patient takes). This places the lateral side of the intramedullary nail, specifically portions of the nail adjacent to the first opening 120 under tension. As described earlier, the angles $\alpha_1$, $\alpha_2$ are selected to distribute stresses applied to the bone fixation device 100 by a trochanteric implant (not shown) inserted through the channel 122 as well as other loads applied to the bone fixation device 100 in use, as those skilled in the art will understand. As those skilled in the art will understand, the exemplary features of the device 100 increase the resistance of the body 102 to fracture. Furthermore, by evenly distributing forces applied thereto, the exemplary device according to the invention may also be formed with a reduced diameter than conventional devices without compromising the strength and life span of the nail, reducing an outer profile of the device and permitting use thereof within a wider user base (e.g., patients having smaller bones requiring bone fixation devices of a smaller profile). However, by virtue of its holding strength, the exemplary device according to the invention may still be used in larger patients without increasing the risk of failure.

An outer wall of the body 102 along the lateral wall 123 may be provided with a facet 150 formed as a lateral relief to reduce stress placed on the device and, consequently, to the bone during insertion. As would be understood by those skilled in the art, the facet described herein may be included on any device 100 with or without either the bumps described above. Specifically, the facet 150 reduces a profile of the nail as it is inserted into the medullary canal with the facet corresponding in location to a portion of the medullary canal which generally includes a curve. Specifically, the facet 150 is configured to permit the body 102 to flex to traverse curvatures in the medullary cavity during insertion. A position of the facet 150 is selected to interface with a greater thickness portion of cortical bone adjacent a trochanter of a femur, as those skilled in the art will understand. Specifically, the facet 150 reduces forced applied to the device 100 by the bone (not shown) and vice versa while still permitting the device 100 to maintain a sufficient holding strength with the bone. The facet 150 extends over a portion of the tapered portion 110 and proximal portion 112 of the body 102. In an exemplary embodiment, the facet 150 extends over the lateral wall 123 of the body 102 so that, when implanted, the facet 150 is in contact with the lateral side of the bone. In another embodiment, an additional facet 150 may be provided on the medial wall 125 of the body 102. The facet 150 may be substantially smooth or may have a plurality of planar walls interfacing one another. It is further submitted that the facet 150 may be formed with any shape and size without deviating from the scope of the present invention. Furthermore, the device 100 may be provided with any number of facets 146 to conform to the requirements of a target bone.

The exemplary device 100 according to the invention may be finished via shot peening although any other cold working process may also be used without deviating from the scope of the invention. As those skilled in the art will understand, the shot peening process may increase a fatigue strength of the device 100, thus permitting the use of a device 100 with a smaller outer profile without compromising a strength thereof. The exemplary system and method according to the invention employs a shot peening process on a substantial portion of the body 102 except the region of the openings 120, 122. This region may be formed via one or more of forging, swaging, rotary swaging, cold-working, heat treatment, or any other process known in the art. In another embodiment, this region may also be finished via shot peening. Thus, the exemplary features of the present invention permit the use of an intramedullary nail having a smaller diameter than used in conventional bone fixation procedures without compromising an overall rigidity of the device 100 within the bone. Rather, the exemplary system and method according to the invention increases a holding strength of the device 100 relative to the bone when compared with larger conventional devices. Specifically, a transverse trochanter screw (not shown) for use with the device 100 may be approximately 0.4 mm smaller than conventional transverse trochanter screws.

FIGS. 6-7 depict a device 200 according to an alternate embodiment of the invention. The device 200 is formed substantially similarly as the device 100 of FIGS. 1-7 with an exception of a faceted portion 250. Specifically, the faceted portion 250 is formed as a plurality of substantially planar walls 250', 250", 250''' provided in proximity to one another. An outer perimeter of the faceted portion 250 is not smooth and may be selected to conform to the anatomy of a target bone, wherein each of the substantially planar walls 250', 250", 250''' may be formed with any length without deviating from the scope of the invention. The device 200 may not comprise an elongated channel 114 extending therethrough and rather, may comprise only a locking hole 260 extending thereinto from the proximal end 106 by a predetermined distance, the locking hole 260 being configured and dimensioned to receive a locking hole therein, as those skilled in the art will understand.

Figure 9:
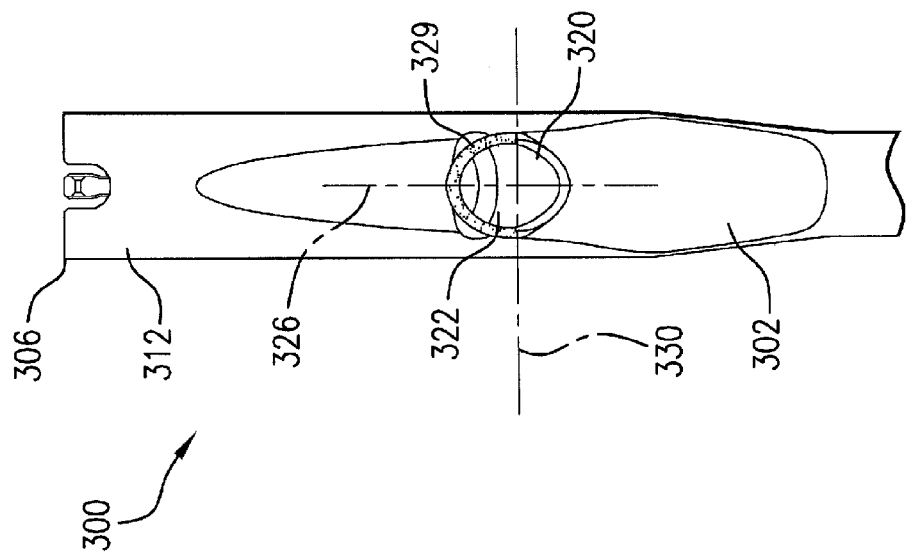
FIG. 9 illustrates a second perspective view of the bone fixation device of FIG. 8.
Figure 8:
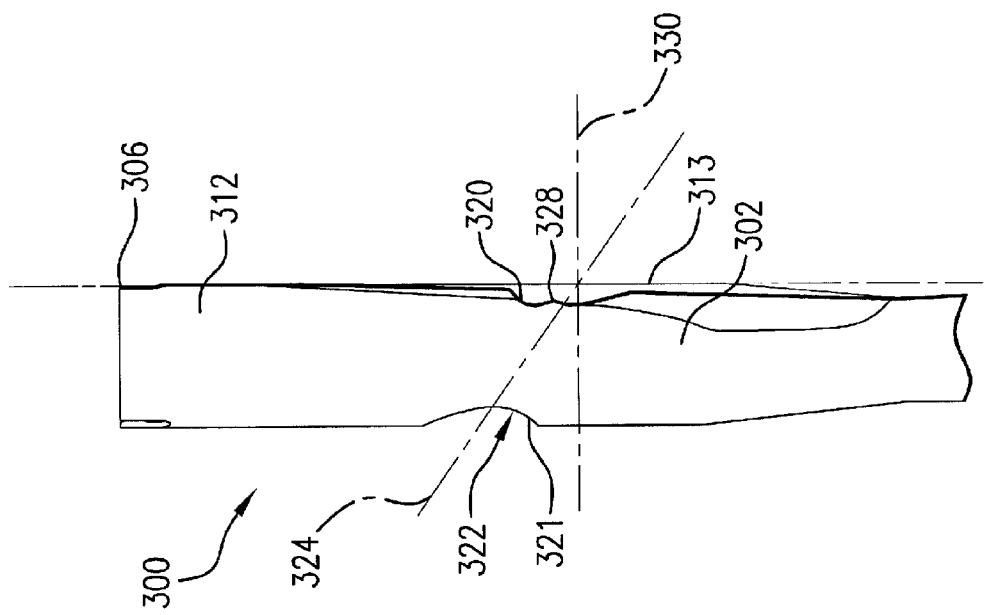
FIG. 8 illustrates a first perspective view of a bone fixation device according to another embodiment of the invention.

FIGS. 8-9 depict a device 300 according to yet another embodiment of the invention. The device 300 is formed substantially similar to the devices 100, 200, except as noted below. The device 300 includes a channel 322 extending along a channel axis 324 and open at ends thereof via first and second openings 320, 321. As with earlier embodiments, a periphery of the second opening 321 may be substantially smooth. A portion of a body 302 adjacent a periphery of the first opening 320 includes a bump 328. The body 302 extends along a longitudinal axis 326. As shown in FIG. 8, an external axis 313 extends along the body 302 extending parallel to the longitudinal axis 326 and aligned with an outer wall of a proximal portion 312 of the body 302. In an exemplary embodiment, the bump 328 is positioned along an edge of the channel 322 proximally of a horizontal line 330 (i.e., toward a proximal end 306 of the body 302), wherein the horizontal line 330 is projected through an intersection of the external axis 313 with the channel axis 324, as shown in FIG. 8. It is further noted that the bump 328 may be positioned anywhere within a region 329 defined proximally of the horizontal line 330. In yet another embodiment, the region 329 any number of bumps 328 may formed therein depending, for example, on the number of locations at which stress concentration would be found in the absence of these bumps. In another embodiment, the region 329 may include one or more pairs of bumps symmetrically disposed about the central longitudinal axis 326.

It will be apparent to those skilled in the art that various modifications and variations may be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A bone fixation device, comprising:
an elongated body having a first channel extending therethrough from a proximal end to a distal end, the elongated body being configured and dimensioned for insertion into a bone;
a first opening formed on a first side wall of the body, the first side wall being configured to face a lateral direction when implanted in a target orientation within the bone;
a second opening formed on a second side wall of the body opposite the first opening;
a second channel extending through the body from the first opening to the second opening along a channel axis, the second channel dimensioned to permit insertion of an implant therethrough;
a first bump disposed on a periphery of the first opening at a location at which a stress concentration would be at a maximum if no such first bump were formed, the first bump being dimensioned to diffuse a concentration of stress about the periphery due to forces applied thereto by an implant extending through the second channel; and
a second bump on the periphery of the first opening, the second bump being dimensioned to diffuse a concentration of stress about the periphery of the first opening due to forces applied thereto by an implant extending through the second channel, wherein the second bump is positioned opposite the first bump,
wherein the first bump is defined by first and second milled portions disposed on first and second sides thereof, each of the first and second milled portions having a radius of curvature selected to diffuse the concentration of stress on the first apex and the first bump is formed between, and the first bump is formed by creation of the first and second milled potions.

2. The bone fixation device of claim 1, wherein the first bump comprises first and second walls extending radially into the first opening joining one another at a first apex of the first bump.

3. The bone fixation device of claim 2, wherein the second bump comprises first and second walls extending radially into the first opening, the first and second walls joining one another at a second apex of the second bump.

4. The bone fixation device of claim 1, further comprising a relief cutout on a side wall of the body, the relief cutout having a reduced cross-sectional profile and being positioned to interface with a reduced clearance portion of a medullary canal into which the device is to be implanted.

5. The bone fixation device of claim 4, wherein the relief cutout is formed with one of a substantially smooth surface and a multi-faceted surface.

6. The bone fixation device of claim 4, wherein the relief cutout is provided on portions of the device which, when the device is implanted in a bone in a desired configuration face laterally and medially.

7. The bone fixation device of claim 1, wherein the second channel is transverse to the first channel.

8. The bone fixation device of claim 1, wherein the device is an intramedullary nail.

9. The bone fixation device of claim 1, wherein the elongated body includes a central longitudinal axis and an external axis extending parallel thereto, the external axis being aligned with an outer wall of the proximal end of the body, wherein the first bump is located on a side of a horizontal axis defined by an intersection of the channel axis with the external axis toward a proximal end of the elongated body.

10. A bone fixation system, comprising:
a device configured for insertion into a bone having an elongated body having a first channel extending distally therein to from a proximal end of the device along a longitudinal axis of the device and a second channel extending transverse to the longitudinal axis between first and second openings, the second channel extending along a channel axis and being dimensioned to permit insertion of an implant therethrough, and a first bump disposed on a periphery of the first opening at a location at which a stress concentration would be at a maximum if no such first bump were formed, the first bump being dimensioned to diffuse a concentration of stress about the periphery due to forces applied thereto by an implant extending through the second channel;
a second bump on the periphery of the first opening, the second bump configured and dimensioned to distribute stresses around the first opening due to forces applied to the device via the implant, the second bump comprising first and second walls extending radially into the first opening away from the periphery of the second opening, the first and second walls joining one another at a second apex of the second bump, wherein the second bump is located opposite the first bump; and
an implant configured for insertion through the second channel,
wherein the first bump is defined by first and second milled portions disposed on first and second sides thereof, each of the first and second milled portions having a radius of curvature selected to diffuse the concentration of stress on the first apex and the first bump is formed between, and the first bump is formed by creation of the first and second milled potions.

11. The system of claim 10, wherein the first bump comprises first and second walls extending radially away from the periphery of the first opening to join one another at a first apex of the first bump.

12. The system of claim 10, further comprising a relief cutout on a side wall of the body, the relief cutout forming a reduced cross-sectional profile portion of the body and being positioned to interface, when the device is implanted to a desired position within a bone, with a reduced clearance portion of a medullary canal of the bone.

13. The system of claim 12, wherein the relief cutout is formed with one of a substantially smooth surface and a multi-faceted surface.

14. The system of claim 12, wherein the relief cutout is provided on surfaces of the body which, when the device is implanted to a desired position within a bone, face laterally and medially.

15. The system of claim 10, wherein the elongated body is configured so that the first opening is positioned adjacent a lateral side of the bone in an operative configuration.

16. The system of claim 10, wherein the elongated body includes an external axis extending parallel to the longitudinal axis, the external axis being aligned with an outer wall of the proximal end of the body, wherein the first bump is located on a side of a horizontal axis defined by an intersection of the channel axis with the external axis toward a proximal end of the elongated body.

* * * * *